United States Patent [19]

Tanguay et al.

[11] Patent Number: 5,329,774
[45] Date of Patent: Jul. 19, 1994

[54] METHOD AND APPARATUS FOR SEPARATING C4 HYDROCARBONS FROM A GASEOUS MIXTURE

[75] Inventors: Dennis C. Tanguay, Stafford, Tex.; Gerard E. Dupuis, Pleasant Hill; Bao Ha, Vacaville, both of Calif.

[73] Assignee: Liquid Air Engineering Corporation, Montreal, Canada

[21] Appl. No.: 958,170

[22] Filed: Oct. 8, 1992

[51] Int. Cl.⁵ ............................................. F25J 3/06
[52] U.S. Cl. .................................... 62/23; 40/335
[58] Field of Search ............................ 62/23, 40, 335

[56] References Cited

U.S. PATENT DOCUMENTS

| | | | |
|---|---|---|---|
| 3,626,705 | 12/1971 | Knapp et al. | 62/23 |
| 3,628,340 | 12/1971 | Meisler et al. | 62/40 |
| 4,229,195 | 10/1980 | Forg | 62/40 |
| 4,256,476 | 3/1981 | Van Baush | 62/23 |

*Primary Examiner*—Ronald C. Capossela
*Attorney, Agent, or Firm*—Young & Thompson

[57] ABSTRACT

A method of and apparatus for separating C4 hydrocarbons from a feed comprising a gaseous mixture. The feed is cooled and partially condensed in a plurality of successive stages of condensation and phase separation. A gaseous overhead from each separation stage is further cooled and supplied to the next separation stage and the liquid separated from each stage is used to cool the gas. Further refrigeration is supplied to the gas to effect the condensations by indirect heat exchange with a closed cycle refrigerant subjected to a compression-/expansion cycle. The feed undergoes no compression and no abrupt expansion during the separation, so that the feed undergoes a pressure decrease due only to friction of the passage of the feed through the apparatus. The pressure loss is no more than about 20 psi. The temperature of the feed is maintained below 150° F. at all times, to prevent polymerization of 1,3-butadiene. A mixed refrigerant passes through the closed refrigeration cycle and contains, in decreasing order of plentitude, propane, ethylene, isopentane and nitrogen. The mixed refrigerant is subjected to a single compression followed by cooling and phase separation. The phases of the mixed refrigerant thus separated are separately cooled and expanded and the material thus produced by expansion is used to cool the feed.

28 Claims, 1 Drawing Sheet

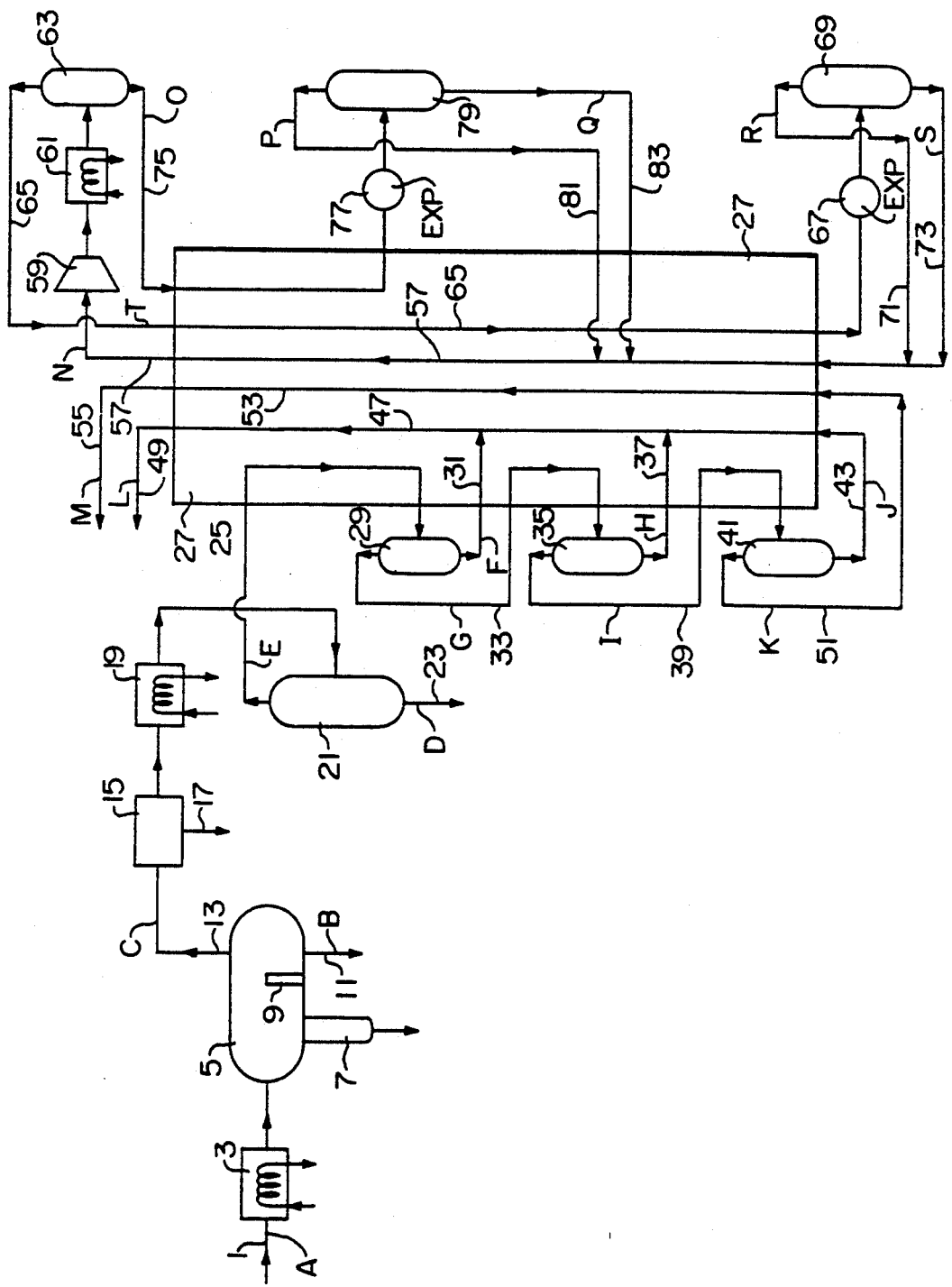

METHOD AND APPARATUS FOR SEPARATING C₄ HYDROCARBONS FROM A GASEOUS MIXTURE

FIELD OF THE INVENTION

The present invention relates to a method and apparatus for separating $C_4$ hydrocarbons, e.g. isobutylene and isobutane, from a gaseous mixture containing the same.

BACKGROUND OF THE INVENTION

It is known to separate $C_4$ hydrocarbons from a gaseous mixture containing the same, by cooling a feed gas partially to condense the same, and to separate organic and aqueous streams from the condensate. The organic fraction is removed from the cycle as product and the aqueous fraction is sewered.

The gaseous fraction is then dried and further cooled thereby partially to condense the same, the liquid phase being removed from the cycle as product and the gaseous phase being compressed to a pressure of about 300 psig.

The compressed gas is cooled in a main heat exchanger, in which it undergoes three stages of partial condensation. The liquid phase from each of the three separations is subjected to Joule-Thomson expansion and returned to the main exchanger to provide refrigeration. The liquid streams thus warmed in the main exchanger are removed from the cycle as product.

In the main exchanger, refrigeration is provided using successively and separately propane and then ethylene as the refrigerant liquids. Further refrigeration is provided by expanding isentropically the vapor remaining from the third operation of phase separation.

However, certain difficulties attend the known process. These are as follows:

1. Among the $C_4$ hydrocarbons is 1,3-butadiene, which polymerizes at temperatures above 150° F. The compression of the feed tends to raise the temperature of the feed above this temperature and bring about this polymerization.

2. The use of separate refrigerants at different temperature levels in the main heat exchanger results in discrete levels of refrigeration and leads to high power consumption.

3. The equipment for compressing the feed gas and for expanding it isentropically complicates the design and operation of the unit and increases its cost.

OBJECTS OF THE INVENTION

It is accordingly an object of the present invention provide a method and apparatus for the separation of $C_4$ hydrocarbons from a gaseous mixture, wherein the maximum temperature of the feed stream at no time exceeds 150° F., thereby to avoid the polymerization of 1,3-butadiene.

Another object of the present invention is the provision of such a method and apparatus, wherein the temperature differences between the feed stream and the refrigerant in a main heat exchanger are kept to a minimum.

It is a further object of the present invention to provide such a method and apparatus, wherein power consumption is kept to a minimum.

The invention also has for an object the provision of such a method and apparatus, wherein pressure change of the feed stream is kept to a minimum and more particularly wherein the feed stream undergoes pressure loss only to the extent of the pressure drop inherent in passage through the apparatus.

A still further object of the present invention is the provision of such a method which will reliably separate $C_4$ hydrocarbons from a gaseous mixture with high accuracy of separation.

Finally, it is an object of the present invention to provide such apparatus which will be relatively inexpensive to construct, reliable and economical to operate, and rugged and durable in use.

SUMMARY OF THE INVENTION

Briefly, the objects of the present invention are achieved by providing a method and apparatus for the separation of $C_4$ hydrocarbons from a gaseous mixture, wherein the gaseous mixture to be separated is subjected to a plurality of partial condensations by cooling, each partial condensation being followed by phase separation and recovery of refrigeration from the separated phase in a main heat exchanger, the feed stream being neither compressed nor expanded but the partial condensations being effected solely by indirect heat exchange with cooling fluids, so that the feed stream undergoes minimum pressure loss, e.g. not more than 20 psi, in the course of the cycle, which pressure loss is due entirely to fluid friction arising from passage of the feed through the apparatus.

The greatest part of the refrigeration load is borne by a closed refrigeration cycle acting in a main heat exchanger, the refrigerant being a mixed refrigerant preferably containing ethylene and propane, more preferably also isopentane, and most preferably also nitrogen. Preferably, the propane is more plentiful in the mixed refrigerant than the other components, the ethylene next most plentiful, the isopentane next most plentiful and finally the nitrogen the least plentiful. This mixed refrigerant is subjected to compression, cooling and phase separation, the liquid phase being subcooled in the main exchanger, expanded isenthalpically and phase separated, the latter separated phases then being returned through the main heat exchanger to provide refrigeration before being recompressed. The vapor phase from the first separation of the cooled compressed closed cycle mixed refrigerant is cooled through the entire heat exchanger, isenthalpically expanded, phase separated, and these latter separated phases are then returned through the entire heat exchanger to the compression step.

BRIEF DESCRIPTION OF THE DRAWING

These and other objects, features and advantages of the present invention will become apparent from a consideration of the following description, taken in connection with the accompanying drawing, which is a cycle diagram of the method and apparatus according to the present invention.

DETAILED DESCRIPTION OF THE INVENTION

Referring now to the drawing in greater detail, there is shown a cycle according to the present invention for the separation of $C_4$ hydrocarbons from a gaseous mixture containing the same, wherein the $C_4$ hydrocarbons are principally isopentane and isobutylene but may also include n-butane, isobutene and 1,3-butadiene. In addition to the $C_4$ hydrocarbons, there may be a major amount of hydrogen and minor amounts of nitrogen, methane and C$_3$ hydrocarbons, namely, propylene and propane, and a minor amount of water.

Typical compositions, temperatures and pressures of the streams throughout the cycle are given in Table 1 at the end of the specification. On the drawing, the reference numerals designate portions of the structure and the reference letters designate points in the cycle whose composition, temperature and pressure are given in Table 1. Thus, particular exemplary compositions, temperatures and pressures will not be given throughout the specification, in order to simplify the specification: instead, they are gathered for convenience in Table 1.

Gaseous feed is introduced through conduit 1 at a temperature and pressure which are the highest temperature and pressure of the feed or any of its separated components throughout the cycle. This temperature is below 150° F., the polymerization temperature of 1,3-butadiene, which accordingly is separated in liquid phase with most of the rest of the C$_4$ hydrocarbons. Similarly, the initial pressure is never increased during the cycle and is diminished during the cycle only by friction losses through the apparatus.

The feed is cooled by an appropriate refrigerant such as propane or ammonia in cooler 3 and is phase separated in a separator 5, water being removed in a water collecting boot 7 and sewered. The liquid hydrocarbons overflow a baffle 9 and are removed at 11 as a cycle product.

The gaseous phase leaves separator 5 at 13 and is subjected to drying at an adsorption-type dryer 15, the removed water being removed at 17 and sewered.

The dried feed in gaseous phase is cooled at 19 by a refrigerant appropriate to its temperature level and partially condensed and phase separated in separator 21, the liquid phase being removed at 23 as product.

The gaseous phase from separator 21 passes through conduit 25 and is cooled in main heat exchanger 27, whereby it is partially condensed and phase separated in separator 29. The liquid phase thus separated is removed through conduit 31 and provides refrigeration for the warm end of exchanger 27.

Preferably, the exchanger 27 is a braised aluminum heat exchanger, although other exchangers such as shell and tube exchangers, plate-fin exchangers, etc. could be used.

The gaseous overhead from separator 29 is passed via conduit 33 through an appropriate temperature level of exchanger 27 wherein it is cooled and partially condensed and phase separated in separator 35. The thus-separated liquid is passed via conduit 37 to main exchanger 27 wherein it supplies refrigeration. The gaseous overhead from separator 35 is removed through conduit 39, cooled and partially condensed at an appropriate temperature level in exchanger 27 and phase separated in separator 41. The condensate thus separated in separator 41 is removed via 43 and is passed through a conduit 47 into which are also fed the condensates from conduits 31 and 37, the thus-warmed stream of combined condensates, still in liquid phase, being removed from the warm end of exchanger 27 via conduit 49.

The gaseous overhead from phase separator 41 is removed by conduit 51 and then fed through a conduit 53 passing entirely through exchanger 27 from the cold end to the warm end thereof, and leaves, of course in vapor phase, at 55.

The material in conduit 49 in liquid phase will be the main product of the separation and will consist principally in C$_4$ hydrocarbons, of which isobutane and isobutylene will together comprise at least about 75%, the next most plentiful component being the C$_3$ hydrocarbons, e.g. propylene and propane.

The gaseous phase leaving at 55 will be predominantly hydrogen but will contain significant percentages of nitrogen and methane.

It is particularly to be noted that, throughout the cycle, the pressure of the feed has nowhere increased, and that overall the pressure of the feed has not decreased by more than the normal friction loss through the apparatus, i.e. not more than about 20 psi. It is also to be noted that the feed can be at any convenient temperature, e.g. ambient, and that it does not rise significantly and in any event remains below 150° F.

It will also be noted that the principal refrigeration of the cycle is provided by the main exchanger 27. For this purpose, exchanger 27 is associated with a closed cycle compression/expansion refrigeration system wherein a mixed refrigerant is used that can be tailored to requirements, and that, in the case of the separation of C$_4$ hydrocarbons, is preferably at least half propane, with ethylene the next most plentiful component, and preferably isopentane in a lesser quantity, and, if desired, nitrogen in a still lesser quantity.

Such a mixed refrigerant passes via conduit 57, in which it has given up its refrigeration to the feed being cooled therein, to a compressor 59 and thence to a cooler 61 cooled by any fluid appropriate to the temperature level in question, e.g. air or water, whereby the compressed refrigerant is partially condensed and separated in a phase separator 63. The gaseous overhead from separator 63 passes via conduit 65 entirely through exchanger 27, from the warm end to the cold end thereof and is isenthalpically expanded in a Joule-Thomson expander 67 and thereby partially condensed, the two phases thus produced being separated in a separator 69. The overhead from separator 69 passes via conduit 71 back to conduit 57 to repeat the cycle; and the condensed liquid from separator 69 passes via conduit 73 to the same conduit 57 for the same purpose.

Returning now to separator 63 for the compressed and cooled refrigerant, the liquid phase refrigerant separated in separator 63 is removed via conduit 75, cooled to an appropriate temperature level in main exchanger 27 and removed therefrom and expanded isenthalpically in a Joule-Thomson expander 77 thereby partially to condense the same. The two-phase refrigerant is then separated in a separator 79, the overhead leaving via a conduit 81 and the condensate leaving via a conduit 83 and both being introduced into conduit 57 for recycling.

Notice that the expansion of the liquid separated in separator 63 is effected at a higher temperature than the expansion of the gaseous overhead separated in separator 63.

The mixed refrigerant closed cycle thus provided for the cooling of exchanger 21, enables the temperature differences between the streams in exchanger 27 to be maintained at a minimum overall average temperature difference, thereby to improve thermal efficiency and reduce the amount of work that needs to be performed to produce the required refrigeration, with consequent saving of cost.

Indeed, a combination of increased thermal efficiency resulting from the absence of compression or abrupt expansion of the feed, as well as the use of a mixed refrigerant in the closed cycle described above, results in a power saving and hence a reduction of the cost of operation of about 5 to 7%, as compared to known arrangements as described at the outset.

It should be particularly noted that with but a single refrigerant, we are able to provide for a single compression of the refrigerant at 59, followed by three different phase separations of that same refrigerant. Thus, the same refrigerant is able to provide refrigeration at plural temperature levels, because the progressive separation of the refrigerant produces in effect different refrigerants each having a different boiling point and hence each having a different position along exchanger 27 at which their separated phases can be appropriately introduced. By suitably selecting the composition of the mixed refrigerant, therefore, plural refrigerant fractions can be produced each of which has a different but predetermined boiling point at the pressure in question. Not only is no more than a single compressor needed, and no isentropic expanders, but also the opportunity is afforded in effect to tailor individual refrigerant mixtures to various temperature levels of the main exchanger. There results not only a reduction in the cost of the equipment and the power to operate it, but also a reduction of the temperature differences along the main exchanger, compared to the prior art described initially.

From a consideration of the foregoing disclosure, therefore, it will be evident that the initially recited objects of the present invention have been achieved.

Although the present invention has been described and illustrated in connection with a preferred embodiment, it is to be understood that modifications and variations may be resorted to without departing from the spirit of the invention, as those skilled in this art will readily understand. Such modifications and variations are considered to be within the purview and scope of the present invention as defined by the appended claims.

TABLE 1

| COMPOSITIONS (mol %), TEMPERATURES AND PRESSURES | | | | | | | | | | |
|---|---|---|---|---|---|---|---|---|---|---|
| | A | B | C | D | E | F | G | H | I | J |
| Hydrogen | 41.87 | 0.64 | 59.63 | 0.62 | 65.98 | 0.59 | 74.18 | 0.47 | 82.16 | 0.43 |
| Nitrogen | 3.17 | 0.10 | 4.49 | 0.11 | 4.96 | 0.12 | 5.57 | 0.14 | 6.16 | 0.16 |
| Carbon monoxide | 0.72 | 0.03 | 1.02 | 0.03 | 1.12 | 0.04 | 1.26 | 0.05 | 1.39 | 0.07 |
| Methane | 3.85 | 0.40 | 5.34 | 0.45 | 5.87 | 0.57 | 6.53 | 1.06 | 7.13 | 1.47 |
| Ethylene | 0.29 | 0.10 | 0.37 | 0.13 | 0.40 | 0.19 | 0.42 | 0.57 | 0.41 | 1.10 |
| Ethane | 0.29 | 0.15 | 0.35 | 0.18 | 0.37 | 0.28 | 0.38 | 0.89 | 0.33 | 1.85 |
| Carbon dioxide | 0.37 | 0.09 | 0.50 | 0.11 | 0.54 | 0.17 | 0.59 | 0.52 | 0.59 | 1.03 |
| Propylene | 3.20 | 4.00 | 2.88 | 4.84 | 2.68 | 6.94 | 2.15 | 15.03 | 0.75 | 26.60 |
| Propane | 1.97 | 2.57 | 1.73 | 3.08 | 1.59 | 4.33 | 1.25 | 8.97 | 0.41 | 15.61 |
| I-butane | 20.67 | 42.41 | 11.95 | 42.64 | 8.33 | 42.46 | 4.05 | 37.91 | 0.38 | 29.25 |
| I-butylene | 21.12 | 45.33 | 11.00 | 43.95 | 7.55 | 40.90 | 3.37 | 31.96 | 0.27 | 21.01 |
| N-butane | 0.40 | 0.94 | 0.18 | 0.83 | 0.11 | 0.67 | 0.04 | 0.40 | — | 0.19 |
| 1-butene | 1.21 | 2.63 | 0.61 | 2.51 | 0.41 | 2.28 | 0.18 | 1.70 | 0.02 | 1.05 |
| 1,3-butadiene | 0.25 | 0.55 | 0.12 | 0.52 | 0.09 | 0.46 | 0.03 | 0.33 | — | 0.18 |
| Pentane | 0.01 | 0.02 | — | — | — | — | — | — | — | — |
| Iso-pentane | — | — | — | — | — | — | — | — | — | — |
| Water | 0.61 | 0.04 | 0.19 | — | — | — | — | — | — | — |
| Temperature, °F. | 100 | 65 | 65 | 45 | 45 | 7.5 | 7.5 | −75.5 | −75.5 | −110.6 |
| Pressure, PSIA | 175 | | | 166 | 166 | | 165 | | 164 | |
| | K | L | M | N | O | P | Q | R | S | T |
| Hydrogen | 83.02 | 0.53 | 83.02 | — | — | — | — | — | — | — |
| Nitrogen | 6.22 | 0.13 | 6.22 | 2.00 | 0.69 | 20.87 | 0.12 | 52.54 | 0.39 | 7.59 |
| Carbon monoxide | 1.41 | 0.05 | 1.41 | — | — | — | — | — | — | — |
| Methane | 7.19 | 0.81 | 7.19 | — | — | — | — | — | — | — |
| Ethylene | 0.40 | 0.38 | 0.40 | 30.28 | 25.13 | 68.77 | 23.91 | 46.21 | 53.17 | 52.22 |
| Ethane | 0.31 | 0.60 | 0.31 | — | — | — | — | — | — | — |
| Carbon dioxide | 0.59 | 0.35 | 0.59 | — | — | — | — | — | — | — |
| Propylene | 0.48 | 11.14 | 0.48 | — | — | — | — | — | — | — |
| Propane | 0.25 | 6.74 | 0.25 | 52.40 | 55.92 | 10.25 | 57.20 | 1.25 | 43.18 | 37.38 |
| I-butane | 0.08 | 40.01 | 0.08 | — | — | — | — | — | — | — |
| I-butylene | 0.05 | 36.33 | 0.05 | — | — | — | — | — | — | — |
| N-butane | — | 0.54 | — | — | — | — | — | — | — | — |
| 1-butene | — | 1.99 | — | — | — | — | — | — | — | — |
| 1,3-butadiene | — | 0.40 | — | — | — | — | — | — | — | — |
| Pentane | — | — | — | — | — | — | — | — | — | — |
| Iso-pentane | — | — | — | 15.32 | 18.26 | 0.11 | 18.77 | — | 3.26 | 2.81 |
| Water | — | — | — | — | — | — | — | — | — | — |
| Temperature, °F. | −110.6 | 50 | 92 | 92 | 110 | −80 | −80 | −132 | −132 | 110 |
| Pressure, PSIA | 163 | — | 162 | 35 | 400 | 35.5 | 35.5 | 35.5 | 35.5 | 400 |

What is claimed is:

1. In a method of separating C4 hydrocarbons from a feed entering separation equipment comprising a gaseous mixture, comprising cooling and partially condensing the feed in a plurality of successive stages of condensation and phase separation wherein a gaseous overhead from each separation stage is further cooled and partially condensed and supplied to the next separation stage and the liquid separated from each said stage is used to cool the gas, and supplying further refrigeration to the gas to effect said condensations by indirect heat exchange with a closed cycle refrigerant subjected to a compression/expansion cycle; the improvement wherein said feed undergoes no compression and no abrupt expansion, whereby said feed undergoes a pressure loss due only to friction of the passage of the feed through all the equipment by which said method is practiced.

2. A method as claimed in claim 1, wherein said pressure loss is no more than about 20 psi.

3. A method as claimed in claim 1, wherein the temperature of the feed is maintained below 150° F. at all times.

4. In a method of separating C$_4$ hydrocarbons from a feed entering separation equipment comprising a gaseous mixture, comprising cooling and partially condensing the mixture in a plurality of successive stages of condensation and phase separation wherein a gaseous overhead from each separation stage is further cooled and partially condensed nd supplied to the next separation stage and the liquid separated from each said stage is used to cool the gas, and supplying further refrigeration to the gas to effect said condensations by indirect heat exchange with a refrigerant subjected to a closed compression/expansion cycle; the improvement wherein said refrigerant is a mixed refrigerant and is subjected to only a single compression throughout said closed compression/expansion cycle.

5. A method as claimed in claim 4, wherein said mixed refrigerant contains at least propane and ethylene.

6. A method as claimed in claim 5, wherein said mixed refrigerant contains a major proportion of propane and a minor proportion of ethylene.

7. A method as claimed in claim 6, wherein said mixed refrigerant contains also isopentane.

8. A method as claimed in claim 7, wherein said mixed refrigerant contains also nitrogen.

9. A method as claimed in claim 4, wherein said mixed refrigerant contains, in decreasing order of plentitude, propane, ethylene, isopentane and nitrogen.

10. A method as claimed in claim 4, comprising subjecting said mixed refrigerant to a single compression followed by cooling and phase separation, and wherein the phases of the mixed refrigerant thus separated are separately cooled and expanded and the material thus produced by expansion is used to cool said feed.

11. A method as claimed in claim 10, wherein the liquid produced by cooling and phase separating the compressed mixed refrigerant is expanded at a higher temperature than the gas produced by cooling and phase separating the compressed refrigerant.

12. A method as claimed in claim 4, wherein said feed undergoes no compression and no abrupt expansion, whereby said feed undergoes a pressure loss due only to friction of the passage of the feed through all the equipment by which said method is practiced.

13. A method as claimed in claim 12, wherein said pressure loss is no more than about 20 psi.

14. A method as claimed in claim 12, wherein the temperature of the feed is maintained below 150° F. at all times.

15. In apparatus for separating C$_4$ hydrocarbons from a gaseous mixture, comprising means for cooling and partially condensing the mixture in a plurality of successive stages of condensation and phase separation wherein a gaseous overhead from each separation stage is further cooled and supplied to the next separation stage and the liquid separated from each said stage is used to cool the gas, and means for supplying a further refrigeration to the gas to effect said condensations by indirect heat exchange with a closed cycle refrigerant subjected to a compression/expansion cycle; the improvement wherein said apparatus is such that said feed undergoes no compression and no abrupt expansion, whereby said feed undergoes a pressure decrease due only to friction of the passage of the feed through all said apparatus.

16. Apparatus as claimed in claim 15, wherein said pressure loss is no more than about 20 psi.

17. Apparatus as claimed in claim 15, wherein the temperature of the feed is maintained below 150° F. at all times.

18. In apparatus for separating C$_4$ hydrocarbons from a feed comprising a gaseous mixture, comprising means for cooling and partially condensing the mixture in a plurality of successive stages of condensation and phase separation wherein a gaseous overhead from each separation stage is further cooled and supplied to the next separation stage and the liquid separated from each said stage is used to cool the gas, and means for supplying further refrigeration to the gas to effect said condensation by indirect heat exchange with a refrigerant subjected to a closed compression/expansion cycle; the improvement wherein said refrigerant is a mixed refrigerant and is subjected to only a single compression throughout said closed compression/expansion cycle.

19. Apparatus as claimed in claim 18, wherein said mixed refrigerant contains at least propane and ethylene.

20. Apparatus as claimed in claim 19, wherein said mixed refrigerant contains a major proportion of propane and a minor proportion of ethylene.

21. Apparatus as claimed in claim 20, wherein said mixed refrigerant contains also isopentane.

22. Apparatus as claimed in claim 21, wherein said mixed refrigerant contains also nitrogen.

23. Apparatus as claimed in claim 18, wherein said mixed refrigerant contains, in decreasing order of plentitude, propane, ethylene, isopentane and nitrogen.

24. Apparatus as claimed in claim 18, comprising means for subjecting said mixed refrigerant to a single compression followed by cooling and phase separation, and means whereby the phases of the mixed refrigerant thus separated are separately cooled and expanded and the material thus produced by expansion is used to cool said feed.

25. Apparatus as claimed in claim 24, wherein the liquid produced by cooling and phase separating the compressed mixed refrigerant is expanded at a higher temperature than the gas produced by cooling and phase separating the compressed refrigerant.

26. Apparatus as claimed in claim 18, wherein said apparatus is such that said feed undergoes no compression and no abrupt expansion, whereby said feed undergoes a pressure decrease due only to friction of the passage of the feed through all said apparatus.

27. Apparatus as claimed in claim 26, wherein said pressure loss is no more than about 20 psi.

28. Apparatus as claimed in claim 26, wherein the temperature of the feed is maintained below 150° F. at all times.

* * * * *